(12) United States Patent
Ortashi et al.

(10) Patent No.: US 10,856,559 B1
(45) Date of Patent: Dec. 8, 2020

(54) METHOD OF PRODUCING EGGSHELL-DERIVED NANOPARTICLES

(71) Applicant: KING SAUD UNIVERSITY, Riyadh (SA)

(72) Inventors: Khalid Mustafa Osman Ortashi, Riyadh (SA); Manal Ahmed Gasmelseed Awad, Riyadh (SA); Awatif Ahmed Hendi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/565,419

(22) Filed: Sep. 9, 2019

(51) Int. Cl.
*A61K 35/57* (2015.01)
*B82Y 40/00* (2011.01)
*A23J 1/08* (2006.01)
*A23P 10/47* (2016.01)

(52) U.S. Cl.
CPC .............. *A23J 1/08* (2013.01); *A23P 10/47* (2016.08); *A61K 35/57* (2013.01); *B82Y 40/00* (2013.01)

(58) Field of Classification Search
None
See application file for complete search history.

(56) References Cited

U.S. PATENT DOCUMENTS

| | | | | |
|---|---|---|---|---|
| 9,480,656 B1* | 11/2016 | Awad | ................... | A61K 9/5073 |
| 9,622,984 B1* | 4/2017 | Virk | ................... | A61K 9/5192 |
| 9,700,512 B1* | 7/2017 | Wagealla | ................... | A61K 9/14 |
| 9,713,624 B1* | 7/2017 | Awad | ................... | A61K 31/7048 |
| 9,789,146 B1* | 10/2017 | Awad | ................... | A61K 36/185 |
| 9,974,750 B1* | 5/2018 | Al-Massarani | ........... | A61K 9/14 |
| 10,202,415 B1* | 2/2019 | El Dib | ................... | C07J 53/002 |
| 10,363,218 B1* | 7/2019 | Virk | ................... | A23K 10/18 |
| 10,398,744 B1* | 9/2019 | Awad | ................... | A61P 1/16 |
| 10,442,833 B1* | 10/2019 | El Dib | ................... | A01N 37/36 |
| 10,500,244 B1* | 12/2019 | Yehia | ................... | A61K 9/1682 |
| 2005/0013868 A1* | 1/2005 | Brynjelsen | ........... | A61K 9/5169 424/489 |

FOREIGN PATENT DOCUMENTS

| | | |
|---|---|---|
| CN | 101926916 A | 12/2010 |
| CN | 106109516 A | 11/2016 |
| CN | 106138174 A | 11/2016 |

OTHER PUBLICATIONS

Habte et al. "Synthesis of Nano-Calcium Oxide from Waste Eggshell by Sol-Gel Method," Sustainability 11:3196, Jun. 7, 2019.*
Hassan et al. "Sonochemical effect on size reduction of CaCO3 nanoparticles derived from waste eggshells," Ultrasonics Sonochemistry 20:1308-1315, 2013 (Year: 2013).*
Render et al., "Development of drug delivery system using bio based calcium carbonate nanoparticles," TechConnect Briefs, vol. 3, May 12, 2013, pp. 312-314.
Chinthakuntla et al., "Calcium Oxide Nano Particles Synthesized From Chicken Egg Shells by Physical Method," International Conference on Emerging Technologies in Mechanical Sciences, Dec. 2014.
Brimeyer, "How to Lower Inflammation, Boost Thyroid and Metabolism, and Protect Yourself from Cancer with Eggshells," Copyright 2019 ForefrontHealth.com, Oct. 18, 2017.

* cited by examiner

*Primary Examiner* — Ileana Popa
*Assistant Examiner* — Alissa Prosser
(74) *Attorney, Agent, or Firm* — Nath, Goldberg & Meyer; Richard C. Litman

(57) ABSTRACT

The method of producing eggshell-derived nanoparticles may include steps of adding eggshell powder to methanol to form a solution; adding the solution dropwise to boiling water under ultrasonic conditions; incubating the resulting solution under continuous stirring at 200-800 rpm; and drying the resulting solution to obtain the eggshell-derived nanoparticles. The method produces nanoparticles of between 5 and 100 nm. Cytotoxicity testing shows that the nanoparticles exhibit anticancer activity against human breast cancer and lung cancer cell lines.

2 Claims, 3 Drawing Sheets

FIG. 1E        FIG. 1F

METHOD OF PRODUCING EGGSHELL-DERIVED NANOPARTICLES

BACKGROUND OF THE INVENTION

1. Field of the Invention

The disclosure of the present patent application relates to nanoparticles exhibiting anticancer activity, and particularly to a method of producing eggshell-derived nanoparticles, the nanoparticles having anticancer activities.

2. Description of the Related Art

Nanoparticles are gaining importance in the fields of biology, medicine and electronics owing to their unique physical and biological properties. The use of environmentally benign materials, such as plant extracts, bacteria, fungi and algae, for the synthesis of nanoparticles offers numerous benefits of eco-friendliness and compatibility with pharmaceutical and other biomedical applications due to the non-toxic nature of the materials involved.

Eggshell is a natural source of calcium and other elements (e.g., strontium and fluorine). Experimental and clinical studies have shown a number of positive properties of eggshell-based material, such as antirachitic effects, in rats and humans. In vitro, eggshell-based materials have been shown to stimulate chondrocyte differentiation and cartilage growth. Clinical and experimental studies have shown that eggshell powder, for example, has positive effects on bone and cartilage and may be suitable in the prevention and treatment of osteoporosis. Possible additional or enhanced medical properties of eggshell-based materials, particularly in the form of nanoparticles, are presently underexplored.

Thus, a method of producing eggshell-derived nanoparticles solving the aforementioned problems is desired.

SUMMARY OF THE INVENTION

A method of producing eggshell-derived nanoparticles may include the steps of adding eggshell in the form of a powder to methanol to form a solution; adding the solution dropwise into boiling water under ultrasonic conditions; incubating the resulting solution under stirring conditions at room temperature; and drying the resulting solution to obtain the eggshell-derived nanoparticles. The eggshell powder nanoparticles prepared according to the presently disclosed method are useful as anticancer agents.

These and other features of the present disclosure will become readily apparent upon further review of the following specification and drawings.

BRIEF DESCRIPTION OF THE DRAWINGS

FIG. 1E shows Transmission Electron Microscopy (TEM) micrographs of exemplary eggshell-derived nanoparticles produced by the present method at a magnification of 200000×.

FIG. 1F shows Transmission Electron Microscopy (TEM) micrographs of exemplary eggshell-derived nanoparticles produced by the present method at a magnification of 300000×.

Similar reference characters denote corresponding features consistently throughout the attached drawings.

DETAILED DESCRIPTION OF THE PREFERRED EMBODIMENTS

Figure 1A:
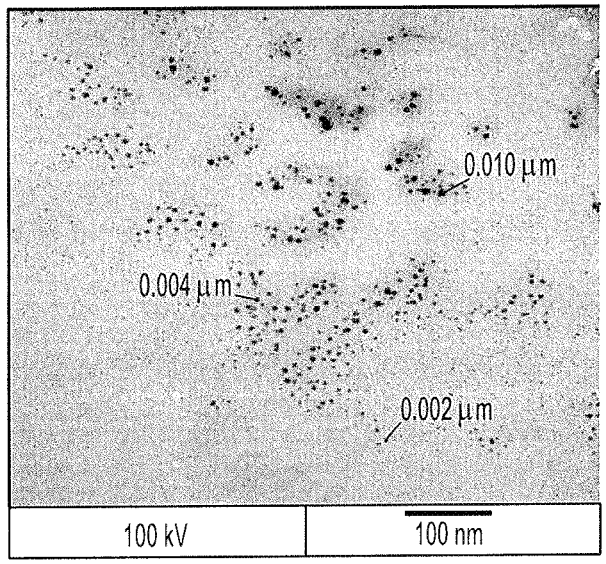
FIG. 1A shows Transmission Electron Microscopy (TEM) micrographs of exemplary eggshell-derived nanoparticles produced by the present method at a magnification of 200000×.
Figure 1B:
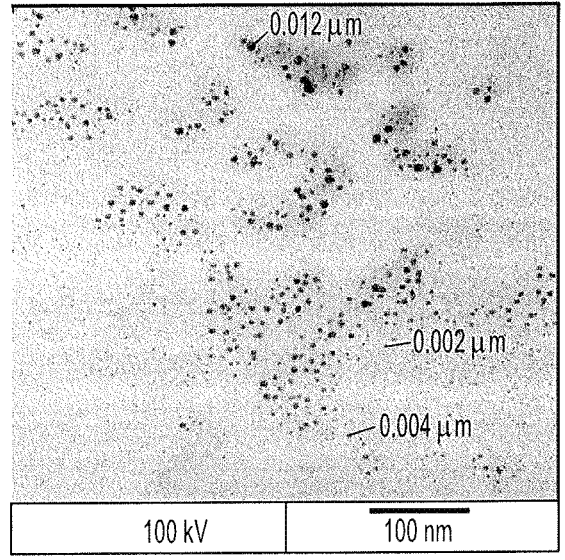
FIG. 1B shows Transmission Electron Microscopy (TEM) micrographs of exemplary eggshell-derived nanoparticles produced by the present method at a magnification of 250000×.
Figure 1C:
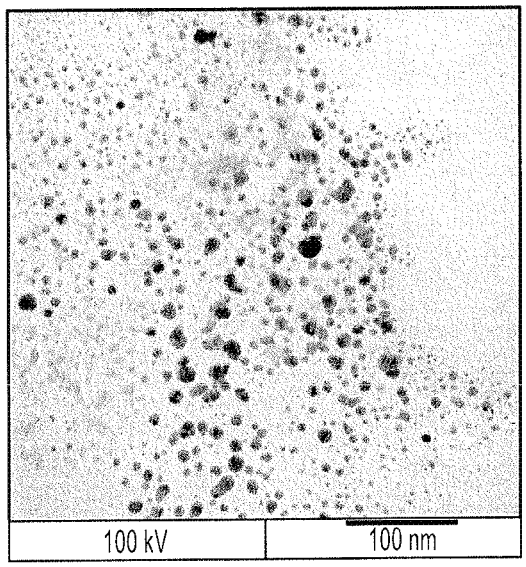
FIG. 1C shows Transmission Electron Microscopy (TEM) micrographs of exemplary eggshell-derived nanoparticles produced by the present method at a magnification of 300000×.
Figure 1D:
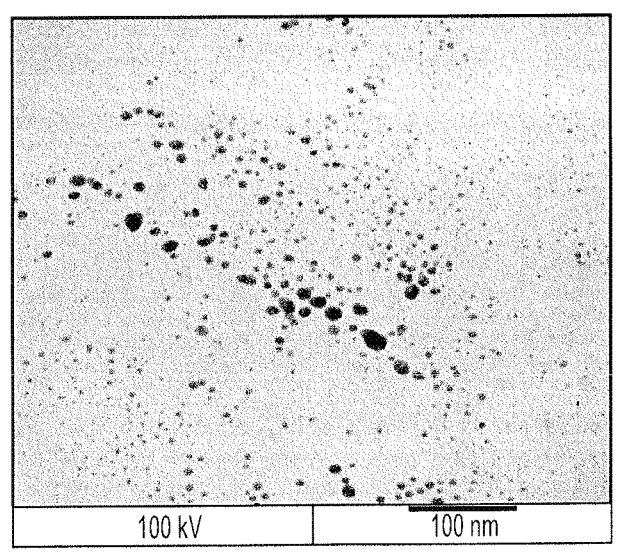
FIG. 1D shows Transmission Electron Microscopy (TEM) micrographs of exemplary eggshell-derived nanoparticles produced by the present method at a magnification of 250000×.

A method of producing eggshell-derived nanoparticles may include the steps of adding eggshell powder to methanol to form a solution; adding the solution dropwise to boiling water under ultrasonic conditions. In an embodiment, the solution is added at a flow rate of about 0.2 mL/min and then sonicated for about 30-60 minutes. The method further includes subsequently incubating the resulting solution under agitation or stirring conditions. The stirring may be continuous at 200-800 rpm and the incubating may be at room temperature for about 10-15 minutes. Finally, the method requires drying the resulting solution to obtain the eggshell-derived nanoparticles. The drying step may include freeze drying.

The present method of synthesizing eggshell-derived nanoparticles provides eggshell-derived nanoparticles with predictable properties and in scalable quantities. The eggshell-derived nanoparticle morphologies can vary, but are typically nearly spherical in shape, and the eggshell-derived nanoparticles produced by the above method may be polydispersed in size.

The method for producing eggshell-derived nanoparticles can be useful in many fields, as the nanoparticles are shown to have anticancer activities, as discussed below. As eggs are an abundant and renewable resource, the present method is particularly desirable for synthesizing eggshell-derived nanoparticles.

It should be understood that the amounts of materials for the methods described herein are exemplary, and appropriate scaling of the amounts are encompassed by the present disclosure, as long as the relative ratio of materials is maintained. As used herein, the term "about," when used to modify a numerical value, means within ten percent of that numerical value. The term "nanoparticle" indicates particles having all dimensions less than 1 micron. The present method is illustrated by the following examples.

In the following examples, we used (Chicken) Hen's white eggshells. The white hen's eggs were obtained from a local market in Riyadh, Saudi Arabia. Eggshells were collected and washed well with tap water and then with distilled water, and then dried by air. Eggshells were broken and crushed into small pieces by grinding in a heavy-duty grinder machine to pass 1-2 mm (the particle size of the starting material) screens to produce eggshell powder.

Example 1

Eggshell-Derived Nanoparticle Synthesis

For the formation of exemplary eggshell-derived nanoparticles, 400 mg of eggshell powder was dissolved in 20 mL methanol to form a solution. The solution was added dropwise into 80 mL of boiling water at a flow rate of 0.2 mL/min over a time period of 5 minutes under ultrasonic conditions, with an ultrasonic power of 750 W and a frequency of 20 kHz. After sonication for 30 min, the contents were stirred at 200-800 rpm at room temperature for about 15 min, and then freeze-dried, resulting in exemplary eggshell-derived nanoparticles.

Example 2

Eggshell-Derived Nanoparticle Characterization

The exemplary eggshell-derived nanoparticles were characterized by transmission electron microscopy (TEM) (JEM-2100F). TEM micrographs of exemplary eggshell-derived nanoparticles are shown in FIGS. 1A-1F. The exemplary eggshell-derived nanoparticle morphologies are typically spherical in shape and polydispersed in size, with average particle sizes ranging between 5 and 100 nm. The TEM images also show the as-produced exemplary eggshell-derived nanoparticles exhibit light agglomeration.

Figure 2:
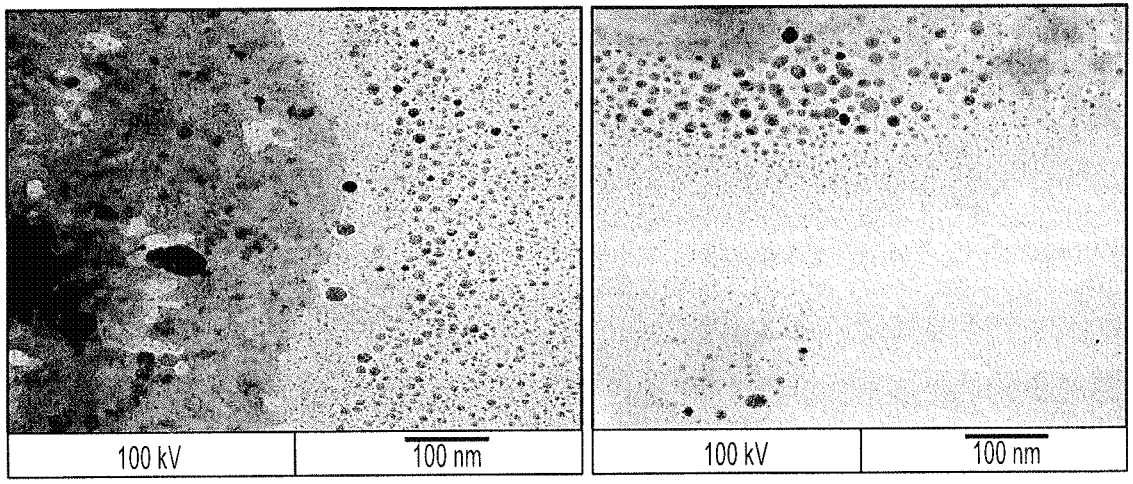
FIG. 2 is a zetasizer plot of the particle size distribution of eggshell-derived nanoparticles produced by the present method.
Figure 2:
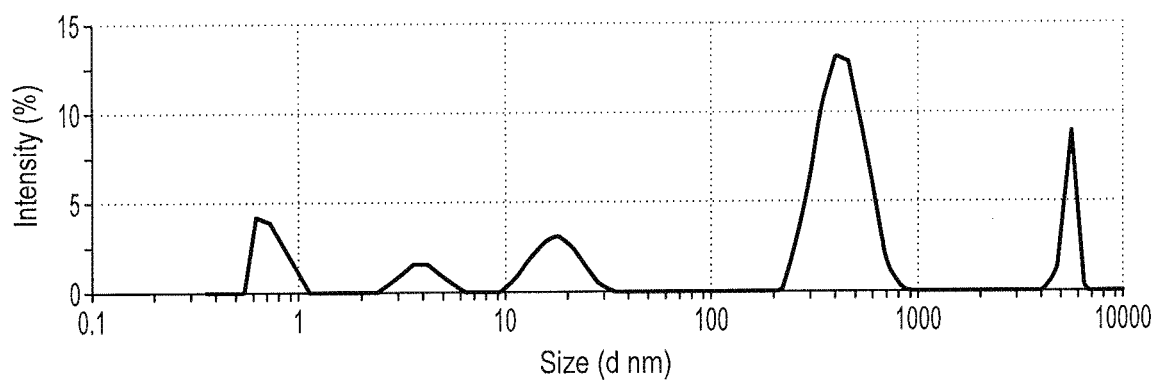

The size distribution of the exemplary eggshell-derived nanoparticles was measured by a Zetasizer, the results of which are shown in FIG. 2. The average size of the exemplary eggshell-derived nanoparticles diameter was found to be between 5 and <100 nm.

Example 3

Evaluation of Cytotoxic Effects of Eggshell-Derived Nanoparticles

Materials used in the following studies showing potential antitumor activities of the exemplary eggshell-derived nanoparticles were as follows.

Mammalian cell lines for in vitro studies: MCF-7 cells (human breast cancer cell line) and A-549 (human lung carcinoma cell line) were obtained from VACSERA Tissue Culture Unit. ACSERA Tissue Culture Unit.

Chemicals Used: Dimethyl sulfoxide (DMSO), crystal violet and trypan blue dye were purchased from Sigma (St. Louis, Mo., USA).

Fetal Bovine serum, DMEM, RPMI-1640, HEPES buffer solution, L-glutamine, gentamycin and 0.25% Trypsin-EDTA were purchased from Lonza. Crystal violet stain (1%): 0.5% (w/v) crystal violet and 50% methanol were made up to volume with $ddH_2O$ and filtered through a Whatmann No. 1 filter paper.

Cell line propagation was performed in Dulbecco's modified Eagle's medium (DMEM) supplemented with 10% heat-inactivated fetal bovine serum, 1% L-glutamine, HEPES buffer and 50 µg/ml gentamycin. All cells were maintained at 37° C. in a humidified atmosphere with 5% $CO_2$ and were subcultured two times per week.

To assess cytotoxicity, a viability assay was performed according to the following. MCF-7 cells or A-549 cells were seeded in a 96-well plate at a cell concentration of $1\times10^4$ cells per well in 100 µl of growth medium. Fresh medium containing different concentrations of the exemplary eggshell-derived nanoparticles was added 24 h after seeding. Specifically, serial two-fold dilutions of the exemplary eggshell-derived nanoparticles in growth medium were added to confluent cell monolayers dispensed into the 96-well, flat-bottomed microtiter plates (Falcon, N.J., USA) using a multichannel pipette. The microtiter plates were incubated at 37° C. in a humidified incubator with 5% $CO_2$ for an additional period of 24 h. Three wells were used for each concentration of the exemplary eggshell-derived nanoparticles. Control cells were incubated without exemplary eggshell-derived nanoparticles and with or without DMSO. The percentage of DMSO present in the wells (at most 0.1%) was found not to affect cell viability.

After incubation with various concentrations of the exemplary eggshell-derived nanoparticles, viable cell yield was determined by a colorimetric method. In brief, after incubation, media were aspirated and crystal violet solution (1%) was added to each well for at least 30 minutes. The stain was removed and the plates were rinsed using tap water until all excess stain was removed. Glacial acetic acid (30%) was then added to all wells, mixed thoroughly, and then the absorbance of the plates was measured after gentle shaking on a Microplate Reader (SunRise, TECAN, Inc., USA) using a test wavelength of 490 nm. All results were corrected for background absorbance detected in wells without added stain. Treated cells were compared to the cell control in the absence of the tested compounds. All experiments were carried out in triplicate.

Figure 3:
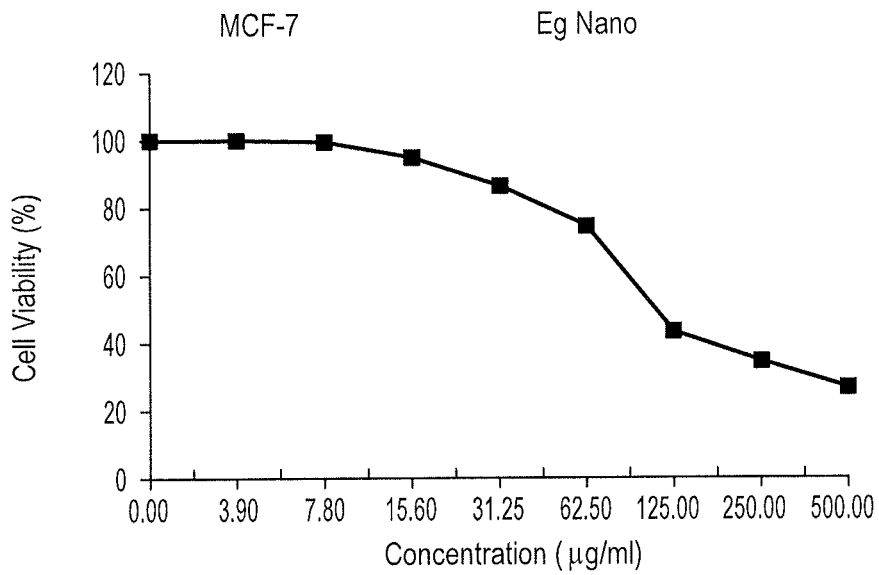
FIG. 3 is a plot of cell viability of the MCF-7 human breast cancer cell line as a function of the concentration of eggshell-derived nanoparticles prepared according to the present method in a suitable solvent.
Figure 4:
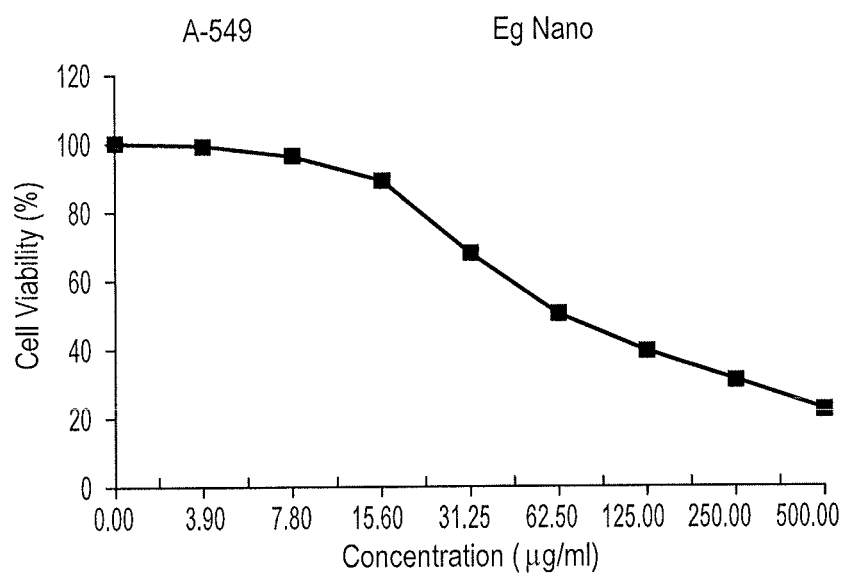
FIG. 4 is a plot of cell viability of the A-549 lung cancer cell line as a function of the concentration of eggshell-derived nanoparticles prepared according to the present method in a suitable solvent.

The cell cytotoxic effect of each tested exemplary eggshell-derived nanoparticles concentration was calculated. The optical density was measured with the microplate reader, as mentioned, to determine the number of viable cells, and the percentage of viability was calculated as $[1-(ODt/ODC)]\times100\%$, where ODt is the mean optical density of wells treated with the exemplary eggshell-derived nanoparticles and ODc is the mean optical density of untreated cells. The relation between surviving cells and drug concentration is plotted to get the survival curve of each tumor cell line after treatment with the specified compound. The 50% inhibitory concentration (IC50), which is the concentration required to cause toxic effects in 50% of intact cells, was estimated from graphic plots of the dose response curve for each concentration using Graphpad Prism software (San Diego, Calif. USA). See FIGS. 3 and 4 for the cytotoxicity effects of the exemplary eggshell-derived nanoparticles on MCF-7 cells and A-549 cells, respectively. The results from all trials are also shown in Tables 1 and 2.

TABLE 1

Inhibitory activity against breast carcinoma cells ($IC_{50}$ = 112 ± 4.61 µg/ml)

| Sample conc. | Viability % (3 Replicates) | | | | Inhibitory | S.D. |
|---|---|---|---|---|---|---|
| (µg/ml) | 1st | 2nd | 3rd | Mean | % | (±) |
| 500 | 29.48 | 25.91 | 24.88 | 26.76 | 73.24 | 2.41 |
| 250 | 36.13 | 34.62 | 32.75 | 34.50 | 65.50 | 1.69 |
| 125 | 47.28 | 42.04 | 40.61 | 43.31 | 56.69 | 3.51 |
| 62.5 | 72.54 | 77.18 | 73.59 | 74.44 | 25.56 | |
| 31.25 | 84.17 | 89.45 | 85.02 | 86.21 | 13.79 | 2.84 |
| 15.6 | 93.86 | 96.31 | 94.16 | 94.78 | 5.22 | 1.34 |
| 7.8 | 98.7 | 100 | 99.43 | 99.38 | 0.62 | 0.65 |

TABLE 1-continued

Inhibitory activity against breast carcinoma cells
($IC_{50}$ = 112 ± 4.61 µg/ml)

| Sample conc. (µg/ml) | Viability % (3 Replicates) | | | | Inhibitory % | S.D. (±) |
|---|---|---|---|---|---|---|
| | 1st | 2nd | 3rd | Mean | | |
| 3.9 | 100 | 100 | 100 | 100 | 0 | 0 |
| 0 | 100 | 100 | 100 | 100 | 0 | |

TABLE 2

Inhibitory activity against lung carcinoma cells
($IC_{50}$ = 64 ± 4.80 µg/ml)

| Sample conc. (µg/ml) | Viability % (3 Replicates) | | | | Inhibitory % | S.D. (±) |
|---|---|---|---|---|---|---|
| | 1st | 2nd | 3rd | Mean | | |
| 500 | 23.28 | 23.14 | 20.32 | 22.25 | 77.75 | 1.67 |
| 250 | 32.04 | 30.61 | 29.58 | 30.74 | 69.26 | 1.24 |
| 125 | 41.27 | 38.94 | 37.82 | 39.34 | 60.66 | 1.76 |
| 62.5 | 48.39 | 53.17 | 49.25 | 50.27 | 49.73 | 2.55 |
| 31.25 | 63.71 | 74.08 | 65.96 | 67.92 | 32.08 | 5.45 |
| 15.6 | 89.64 | 91.72 | 85.44 | 88.93 | 11.07 | 3.20 |
| 7.8 | 98.4 | 96.83 | 93.72 | 96.32 | 3.68 | 2.38 |
| 3.9 | 100 | 99.15 | 98.45 | 99.20 | 0.80 | 0.78 |
| 0 | 100 | 100 | 100 | 100 | 0 | |

It is to be understood that the method of producing eggshell-derived nanoparticles is not limited to the embodiments described above, but encompasses any and all embodiments within the scope of the following claims.

We claim:

1. A method of producing eggshell-derived nanoparticles having cytotoxic effect on mammalian cell lines consisting of the steps of:

adding eggshell powder to methanol to form a solution;

adding the solution dropwise to boiling water at a flow rate of about 0.2 mL/min and then sonicating for about 30-60 minutes;

incubating the resulting solution with continuous stirring at 200-800 rpm at room temperature for about 10-15 minutes; and drying the resulting solution to obtain the eggshell-derived nanoparticles, wherein the nanoparticles have a spherical shape and an average size of less than 100 nm.

2. The method of producing eggshell-derived nanoparticles according to claim 1, wherein the step of drying the resulting solution is freeze-drying.

* * * * *